US007458958B2

(12) United States Patent
Worsoee

(10) Patent No.: US 7,458,958 B2
(45) Date of Patent: *Dec. 2, 2008

(54) OSTOMY SUPPORT GARMENT

(75) Inventor: Blarne Worsoee, Tikoeb (DK)

(73) Assignee: Coloplast A/S, Humlebaek (DK)

( * ) Notice: Subject to any disclaimer, the term of this patent is extended or adjusted under 35 U.S.C. 154(b) by 52 days.

This patent is subject to a terminal disclaimer.

(21) Appl. No.: 10/542,939

(22) PCT Filed: Feb. 3, 2004

(86) PCT No.: PCT/DK2004/000073

§ 371 (c)(1),
(2), (4) Date: Jul. 21, 2005

(87) PCT Pub. No.: WO2004/069116

PCT Pub. Date: Aug. 19, 2004

(65) Prior Publication Data

US 2006/0135919 A1 Jun. 22, 2006

(30) Foreign Application Priority Data

Feb. 3, 2003 (DK) .............................. 2003 00143
Sep. 30, 2003 (DK) .............................. 2003 01428

(51) Int. Cl.
 A61F 5/44 (2006.01)
(52) U.S. Cl. ..................... 604/345; 604/338; 604/339
(58) Field of Classification Search ................. 604/345, 604/338, 339
See application file for complete search history.

(56) References Cited

U.S. PATENT DOCUMENTS

| 2,688,327 | A | * | 9/1954 | Berg ........................... 604/333 |
| 3,468,310 | A | | 9/1969 | Kimball |
| 3,773,048 | A | * | 11/1973 | Kirkliauskas ............... 604/345 |
| 4,495,662 | A | | 1/1985 | Miller |
| 4,533,355 | A | | 8/1985 | Fair |
| 4,888,006 | A | | 12/1989 | Beaupied |
| 5,135,520 | A | * | 8/1992 | Beaupied ..................... 604/345 |
| 5,626,570 | A | | 5/1997 | Gallo |
| 5,843,054 | A | | 12/1998 | Honig |
| 6,014,777 | A | | 1/2000 | Gupton |
| 6,110,156 | A | * | 8/2000 | Mendonca .................. 604/345 |
| 6,202,222 | B1 | | 3/2001 | Robbins |
| 6,468,254 | B2 | * | 10/2002 | Gupton ....................... 604/345 |
| 6,635,050 | B1 | | 10/2003 | Jensen et al. |
| 2002/0016578 | A1 | | 2/2002 | Gupton |

FOREIGN PATENT DOCUMENTS

| DE | 295 15 486 | 9/1995 |
| DE | 100 51 080 | 3/2002 |
| DK | 174536B B1 | 5/2003 |
| WO | WO 00/67683 | 11/2000 |

* cited by examiner

Primary Examiner—Jacqueline Stephens
(74) Attorney, Agent, or Firm—Jacobson Holman PLLC

(57) ABSTRACT

An ostomy support garment in the form of a material having a hole for receiving a stoma, said hole having a stabilized edge wherein the edge is provided with an element allowing an increase or reduction of the length of the edge of the hole and providing a snug fit to the stoma ensures an easy application and removal of the garment and of a collecting bag combined with a sufficient support next to the stoma.

20 Claims, 2 Drawing Sheets

OSTOMY SUPPORT GARMENT

This is a nationalization of PCT/DK2004/000073 filed 3 Feb. 2004 and published in English.

BACKGROUND OF THE INVENTION

Field of the Invention

The present invention relates to an ostomy support garment having a hole for receiving a stoma and more particularly to an ostomy support garment having an adjustable hole for receiving a stoma.

In connection with surgery for a number of diseases in the gastrointestinal tract a consequence is, in many cases that the colon, the ileum or the urethra has been exposed surgically and the patient is left with an abdominal stoma. Such artificial openings or fistulae cannot be controlled at will and are therefore of necessity incontinent and the effluents or waste products of the body, which are conveyed through these organs, are discharged through the artificial orifice or opening and are collected in a collection bag. Said bag is usually adhered to the skin by means of an adhesive wafer or plate having an inlet opening for accommodating the stoma. Such appliances may be two-piece or one-piece appliances. In both types of appliances, a body side member is attached to the wearer's abdomen, and a receiving member or bag is attached to the body side ostomy member for receiving exudates from the stoma. Said receiving member being attached releasably in case of a two-piece appliance.

In many instances patients having had a surgery resulting in the formation of a stoma, an accompanying condition is formation of a peristomal bulge or hernia, which may complicate the bandaging of the stoma and even require further surgery. Even if further surgery is carried out there is a considerable risk of a permanent condition, which cannot be alleviated.

In such cases, the patient will have to rely on an additional hernia support for a mechanical reposition of the bulge or hernia for reducing the risk of constriction or strangulation calling for urgent surgery and for providing a plane surface around the stoma for application of a collecting appliance in order to secure a proper adherence and sealing. Stomal bulge or hernia supports are commonly known and may e.g. be in the form of a belt of e.g. of leather with buckles or in the form of a support garment made from an elastic fabric being able to apply a sufficient pressure around the stoma.

In the case of a colostomy and in case the ostomate is normally irrigating, a minor cap or collecting bag may be used which enables the use of a firm support belt or tight compression briefs for providing a sufficient pressure around the stoma. For ileostomates or urostomates this procedure is not practicable due to the constant rather high output from the ileum or bladder and for urostomates it may be critical to provide a free flow from the stoma in order to prevent a build-up of a backpressure, which may destroy the kidneys.

In such cases, it is highly desirable or mandatory to give access to a larger collecting volume, which means that the collecting bag itself will have to be situated outside the pressure establishing belt or briefs and that a passageway through the same has to be established.

Determination of the site for placing the stoma is normally carried out prior to the operation after observing the patient in different postures, e.g. sitting, standing and bending over, finding the less critical area. WO 00/67683 discloses a device for use in the determination of the optimum position of a stoma-to-be for the patient in question.

As the placing of a stoma is not standardised but depends on the condition and the topography of the abdominal area of the patient, it is not possible to provide a simple selection of standard bulge or hernia supports fitting the majority of patients. The passageways must be tailored according to the actual conditions of the individual patient.

When making a hole in an ostomy support garment it has to be considered that the supporting effect of the missing material has to be provided for in another way and furthermore, it is necessary to stabilise the edge of a hole in order to avoid that it is inadvertently enlarged. At the same time, the effect of the stretching of the support garment and deformation of the shape of the hole when applied has to be taken into consideration as well as the problems associated with providing a sufficiently large hole for allowing an easy passing of an ostomy collection bag during application and removal of the garment and the passing of intestinal contents from the stoma into the bag and at the same time providing a sufficiently snug fit to the stoma to ensure the support next to the stoma.

2. Description of the Related Art

DK Patent Application No. PA 1999 01559 discloses a stomal hernia support compression garment in the form of a pair of compression trousers having a customised hole. The edge of the hole is stabilised by incorporation of a string of nylon sewn with a lockstitch and a zigzag stitch to ensure that the shape of the hole is not changed and furthermore, an enforcement of cotton is sewn using zigzag stitch for stabilising the area around the hole.

U.S. Pat. No. 5,135,520 discloses a variable closure device for an ostomy garment having a pair of crisscross pocket forming panels configured to lie behind an ostomy device. The crisscross arrangement of pocket panels are created by finished edges which overlap along their lower ends to define an adjustable, elongated, slanted slot.

It is an object of the present invention to provide a hernia supporting device which provides a hole through which an ostomy bag may be passed, but which is shaped such that the bag is not moved out of the hole by accident. Thus it is an object to provide a supporting device which provides a snug fit between an edge of a hole in the supporting device and the ostomy bag.

It is also an object of the present invention to provide a hole which is flexible so as to make it easier for the user to pass the ostomy bag through the hole and such that the hole adapts to the shape of the ostomy device.

SUMMARY OF THE INVENTION

The present invention relates to an ostomy support garment having a hole for receiving a stoma, said hole having a stabilised and adjustable edge.

BRIEF DESCRIPTION OF THE DRAWINGS

The invention is disclosed more in detail with reference to the drawings in which.

DETAILED DESCRIPTION OF THE PRESENT INVENTION

Figure 1:
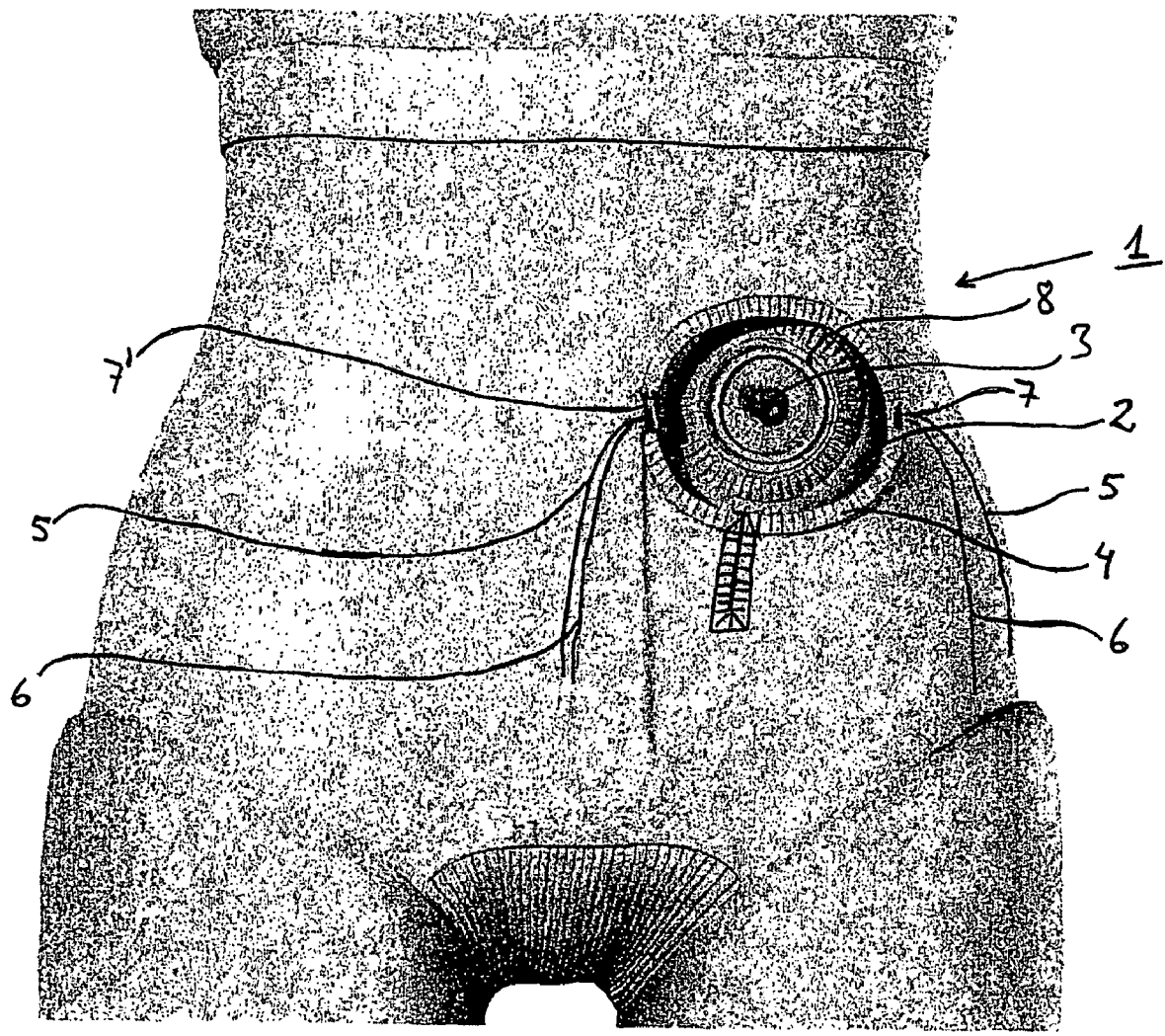
FIG. 1 shows an embodiment of the invention in the form of a pair of support briefs worn by a user.

The present invention relates to an ostomy support garment in the form of a material having a hole for receiving a stoma, said hole having a stabilised edge wherein the edge is provided with an element allowing an increase or reduction of the length of the edge of the hole, wherein the hole is provided with a slit, which juts from the edge of the hole into the material and the element is a fastening element enabling a closure of the slit reducing the perimeter of the hole.

It may be seen as an advantage of the present invention that the hole (and its edge) is flexible and stable enough to support the ostomy bag. Had the edge of the hole been inflexible it would be harder to pull the ostomy bag through the hole, as the hole could not be temporarily enlarged. Furthermore an unflexible hole could not follow the movement of the user and thus an edge of the hole would apply unwanted pressure to the ostomy bag for some positions of the user e.g. when sitting down or when bending forward.

It may further be seen as an advantage of the present invention that the slit provides the possibility of temporarily making the hole bigger, such that an ostomy bag may be passed through the supporting device. When this is done the sides of the slit may be moved towards each other e.g. such that they abut on each other.

When removing the fastening element temporarily, the hole may easily be enlarged and obtain a keyhole shape facilitating the application and removal of the garment or a collecting bag. Then, the fastening element is repositioned closing the slit and providing a snug fit to the stoma and a sufficient support next to the stoma. In this embodiment, the increase or reduction of the length is not depending on elasticity of the material from which the garment is made. Thus, also non-elastic materials may be used without jeopardizing the facility of the application and removal of the garment or a collecting bag.

By changing the effective length of the edge of the hole, the size of the hole may be temporarily increased and/or the shape of the hole may be temporarily changed for facilitating the application or removal of the garment or a collecting bag. By length of the edge of the hole is meant the length of the perimeter of the hole i.e. the distance along the inner edge of the hole. The cross-sectional area of the hole may be made bigger by increasing the length of the edge. However for the same length of the edge of the hole, the cross-sectional area may vary as a circular hole has bigger area than an elliptic hole.

In one embodiment, the fastening is an element closing the slit is suitably a lace placed in a passage at the edge of the hole, said passage being interrupted by the slit. When untying the lace, the hole may be enlarged and obtain a keyhole shape and the size of the hole is reduced by tying a knot or bow drawing the ends of the passage together providing a snug fit to the stoma.

In the alternative, the fastening closing the slit is a zip-like fastener drawing the edges of the slit together or snaps, buckles, buttons, rings or by mating elements of hook and loop fastening material bridging the slit at the edge of the hole.

If the fastenings closing the slit are able to take up the stretching forces of the garment when applied, the slit may stretch from the edge of the hole to the waste-line of the garment facilitating the application and removal of the garment. The garment of the invention has a hole having a stabilised edge being sufficiently stiff and providing a snug fit to the stoma to ensure a sufficient support next to the stoma and also enabling an easy application and removal of the garment or a collecting bag.

The supporting device of the present invention may be mass-produced in different sizes and with different positions of the hole. However the best fit is provided by customising the device and the hole the user of the device. Such customisation makes it possible to provide an even closer fit between the edge of the hole and the ostomy bag as the hole is positioned in exactly the right spot.

In relation to the present invention it may be usefull that the garment is made from an elastic material and the element is a string attached to the edge in a manner allowing an increase or decrease of the perimeter of the hole. When tightening the string, a snug adaptation of the size of the hole to the stoma is obtained together with a sufficient support next to the stoma and when loosening the string, an enlargement of the size of the hole is obtained which facilitates the application and removal of the garment or a collecting bag.

It is usefull in connection with the present invention that the element is a cord placed in a passage at the edge of the hole. The use of a passage stabilises the edge and allows for a continuous adaptation of the length of the edge of the hole.

The use of a passage in the edge of the hole stabilises said edge and allows for a continuous adaptation of the length of the edge of the hole. The passage may extend along the entire edge of the hole or may be divided into a plurality of passages distributed along the edge. If a plurality of passages are provided it may be easier for the user to replace a broken cord as the user need not to mingle a cord through a long passage without being able to pull the cord most of the way. On the other hand a continuous cord provides the best fit between the device and the ostomy bag.

It may be practical that the element is forming a lace giving the option of a simple fixation of the length by tying a knot or bow or by locking the ends of the cord using a cord lock when the ends of the cord have a common exit from the passage. This embodiment gives a simple loosening and fixation of the cord(s) and adaptation of the length of the rim of the hole, especially for users having poor dexterity.

Useful in connection with the present invention is that the element is in the form of two cords having two common exits from the passage, preferably situated spaced about 180° from each other, the cords passing through complementary parts of the passage and each set of two ends of the cords having the common exits from the passage being locked using a cord lock.

It may be seen as practical that the element is an elastic element which together with the elasticity of the material from which the garment is made allows for a temporary enlargement of the hole without having to rely on untying and tying a string or lace. An elastic element is suitably an elastic band such as a band of rubber, cord fabric, or cavalry twill.

DESCRIPTION OF THE PREFERRED EMBODIMENTS

The invention is now explained more in detail with reference to the drawings showing preferred embodiments of the invention.

Reference is made to FIG. 1 showing an embodiment of an ostomy support garment of the invention in the form of a pair of support briefs 1 worn by a user, said briefs having a hole 2 for receiving a stoma 3, said hole having a stabilised edge 4 wherein the edge is in the form of a passage in which are placed two cords 5,6 leaving the passage through two common exits from the passage situated spaced about 180° from each other, each of the cords passing through complementary parts of the passage and each set of two ends of the cords having common exits from the passage being locked using a cord lock 7,7'. An ostomy body side member 8 is placed on the abdomen of the user for attachment of a collecting bag.

Figure 2:
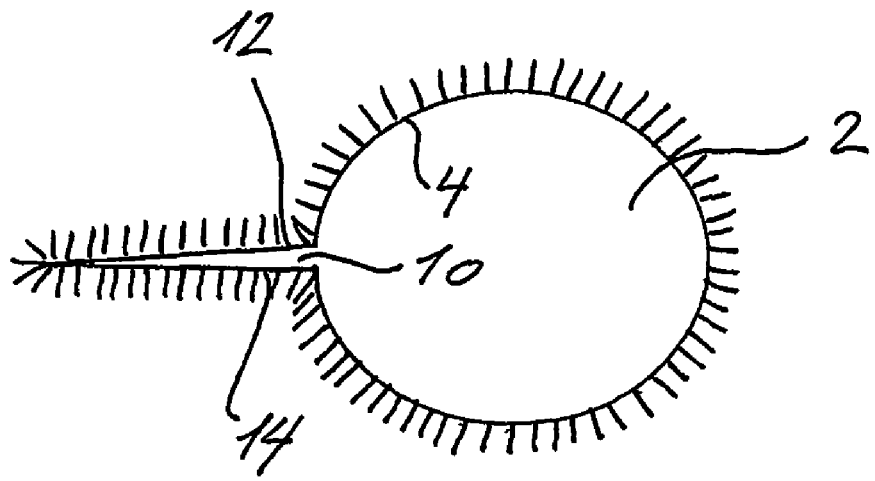
FIGS. 2 and 3 show different configurations of the slits.
Figure 3:
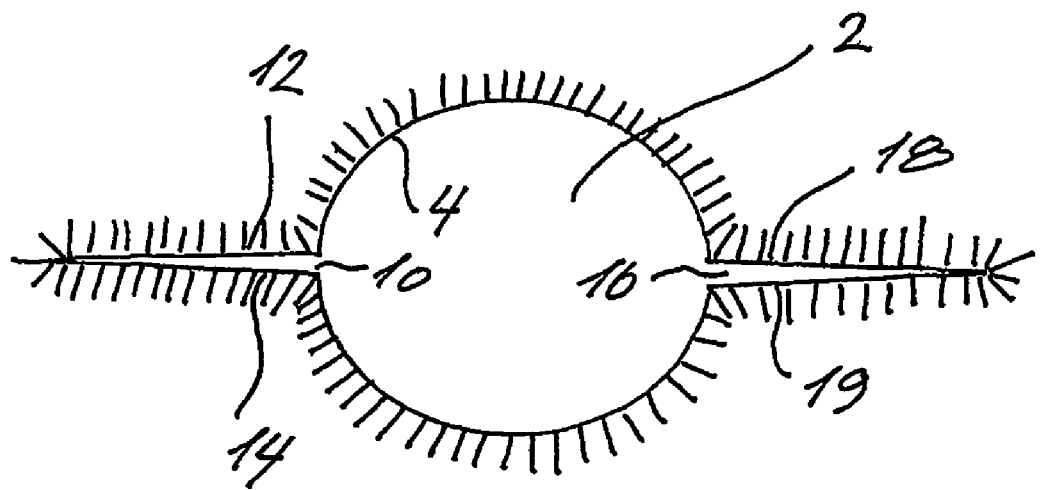

FIGS. 2 and 3 show different embodiments of the slits (10, 16) of the present invention. In FIG. 2 one slit 10 is provided in the stabilised edge 4 of the hole 2. The slit has a first side 12 and a second side 14. The first side 12 and the second side 14 may be made such that they abut on each other or a gab may be provided between the two sides. In FIG. 3 a first slit 10 and a second slit 16 are provided each having first sides (12, 18) and second sides (14, 19).

The invention claimed is:

1. An ostomy support garment comprising a portion of material fabricated to apply pressure against a wearer's skin to provide support to a stoma, said portion of material having a through-passing hole going from inside of said garment to an outside thereof, said hole being positioned over the stoma and having a perimeter sized to encircle the stoma while leaving the stoma and an area surrounding said stoma exposed through the hole when the garment is being worn, said hole perimeter having a stabilized edge that is provided with an element configured to allow the perimeter of the hole to be increased and decreased to enlarge and reduce, respectively, the exposed area surrounding the stoma, said material having at least one slit cut therethrough that adjoins the hole and splits said edge to enlarge said hole by opening said slit, and said element being configured to close the slit to reduce the perimeter of the hole.

2. The garment as set forth in claim 1, wherein the element closing the slit is a lace placed in a passage at the edge of the hole, said passage being interrupted by the slit.

3. The garment as set forth in claim 1, wherein the element closing the slit is selected from the group consisting of zip-like fasteners, snaps, buckles, buttons, rings, and mating elements of hook and loop fastening material bridging the slit at the edge of the hole.

4. The garment as set forth in claim 1, further comprising a pair of slits that each cut through the garment material and the stabilized edge.

5. The garment as set forth in claim 4, wherein said pair of slits are positioned approximately opposite one another around the perimeter of the hole.

6. The garment as set forth in claim 5, wherein the stabilized edge includes a passage with openings adjacent each of the slits, said element including two cords respectively threaded through complementary parts of the passage and secured to one another when extended through the openings to fix the size of the hole perimeter.

7. The garment as set forth in claim 1, wherein the garment material is an elastic material to support the stoma and the element is an elastic lace threaded through a passage formed in said stabilized edge such that the size of the perimeter can be temporarily enlarged without unfastening the elastic lace.

8. The garment as set forth in claim 1, wherein said slit is cut through said material from the inside of the garment to the outside thereof such that, when said slit is opened, the hole is enlarged and a greater portion of the area surrounding the stoma is visible from outside the garment.

9. An ostomy support garment comprising a material providing support to a stoma and having a hole therein that goes entirely through said garment from an outside of the garment to an inside thereof, said hole being positioned over the stoma and having a perimeter sized to encircle the stoma while leaving the stoma and an area surrounding the stoma exposed through the hole when the garment is being worn, said hole perimeter having a stabilized edge that is provided with an element configured to cooperate with the stabilized edge to allow the perimeter to be increased to a size sufficient for an ostomy bag to be passed through the garment hole and also to be reduced to more closely surround and provide support next to the stoma, said stabilized edge being split at least once by a slit that extends from the edge of the hole into the material to enlarge the hole by opening said slit, and said element being configured to close the slit to reduce the perimeter of the hole.

10. The garment as set forth in claim 9, wherein the element closing the slit is a lace placed in a passage at the edge of the hole, said passage being interrupted by the slit.

11. The garment as set forth in claim 9, wherein the element closing the slit is selected from the group consisting of zip-like fasteners, snaps, buckles, buttons, rings, and mating elements of hook and loop fastening material bridging the slit at the edge of the hole.

12. The garment as set forth in claim 9, further comprising a pair of slits that each cut through the garment material and the stabilized edge.

13. The garment as set forth in claim 12, wherein said pair of slits are positioned approximately opposite one another around the perimeter of the hole.

14. The garment as set forth in claim 13, wherein the stabilized edge includes a passage with openings adjacent each of the slits, said element including two cords respectively threaded through complementary parts of the passage and secured to one another when extended through the openings to fix the size of the hole perimeter.

15. The garment as set forth in claim 9, wherein the garment material is an elastic material to support the stoma and the element is an elastic lace threaded through a passage formed in said stabilized edge such that the size of the perimeter can be temporarily enlarged without unfastening the elastic lace.

16. The garment as set forth in claim 9, wherein said slit is cut through said material from the inside of the garment to the outside thereof forming two free edges such that, when said slit is opened, the hole is enlarged and a greater portion of the area surrounding the stoma is visible from outside the garment.

17. The garment as set forth in claim 16, wherein said free edges are in non-overlapping abutment with one another when the slit is closed and are spaced from one another when said slit is opened, the spacing between said free edges when the slit is opened being greatest adjacent said hole and narrowing toward an opposite end of said slit.

18. An ostomy support garment comprising a material providing support to a stoma and having a through-passing hole going from an inside of said garment to an outside thereof, said hole being positioned over the stoma and having a perimeter sized to encircle the stoma while leaving the stoma and an area surrounding said stoma exposed through the hole when the garment is being worn, said hole perimeter having a stabilized edge with at least one slit cut through said edge and an adjoining portion of said material from the inside of the garment to the outside thereof to form two free edges on either side of said slit, said hole being enlarged and a greater portion of the area surrounding the stoma being visible from outside the garment when said slit is opened.

19. The garment as set forth in claim 18, wherein said free edges are in non-overlapping abutment with one another when the slit is closed and are spaced from one another when said slit is opened.

20. The garment as set forth in claim 18, wherein when the slit is opened the spacing between said free edges is greatest adjacent said hole and narrows toward an opposite end of said slit.

\* \* \* \* \*